United States Patent [19]

Gueret et al.

[11] Patent Number: 5,830,485
[45] Date of Patent: Nov. 3, 1998

[54] COLORED COSMETIC COMPOSITION

[75] Inventors: Jean-Louis H. Gueret; Jean-Pierre Arraudeau, both of Paris, France

[73] Assignee: L'Oreal, Paris, France

[21] Appl. No.: 864,111

[22] Filed: May 28, 1997

Related U.S. Application Data

[63] Continuation of Ser. No. 564,727, Nov. 29, 1995, abandoned, which is a continuation of Ser. No. 219,891, Mar. 30, 1994, abandoned.

[30] Foreign Application Priority Data

Apr. 6, 1993 [FR] France ................................. 93 04061

[51] Int. Cl.$^6$ ..................................................... A61K 7/48
[52] U.S. Cl. ........................... 424/401; 424/61; 424/63; 424/69; 424/78.02; 424/78.03
[58] Field of Search ........................... 424/401, 61, 70.1, 424/70.8, 63, 69, 78.02, 78.03

[56] References Cited

U.S. PATENT DOCUMENTS

| | | | |
|---|---|---|---|
| 4,919,922 | 4/1990 | Miyoshi et al. | 424/63 |
| 4,962,130 | 10/1990 | Yanagida et al. | 514/846 |
| 5,320,835 | 6/1994 | Pahlck et al. | 424/64 |
| 5,382,433 | 1/1995 | Pahlck et al. | 424/401 |

FOREIGN PATENT DOCUMENTS

| | | |
|---|---|---|
| 0279319 | 8/1988 | European Pat. Off. . |
| 9104093 | 4/1991 | European Pat. Off. . |
| 0504066 | 9/1992 | European Pat. Off. . |
| 2563104 | 10/1985 | France . |
| 2651789 | 3/1991 | France . |
| 2664160 | 1/1992 | France . |
| 1169323 | 11/1969 | United Kingdom . |
| 9106277 | 5/1991 | WIPO . |
| 9216190 | 10/1992 | WIPO . |

*Primary Examiner*—Jyothsna Venkat
*Attorney, Agent, or Firm*—Nixon & Vanderhye

[57] ABSTRACT

Coloured cosmetic composition containing at least one particulate filler and at least one colorant, in which at least part of the fillers of the composition is coated with a polymer combined with at least one colorant.

1 Claim, No Drawings

5,830,485

COLORED COSMETIC COMPOSITION

This is a continuation of application Ser. No. 08/564,727, filed on Nov. 29, 1995, which was abandoned upon the filling hereof, which is a con of Ser. No. 08/219,891, filed Mar. 30, 1994, abandoned.

The present invention relates to a colored cosmetic composition containing a particulate filler.

It is known to prepare colored cosmetic compositions containing solid particulate fillers. These cosmetic compositions are, in particular, lipsticks, loose or compacted powders, make-up foundations in cream form, rouges or blushers, eyeliners, eyeshadows, mascaras or nail varnishes.

In the above compositions, the fillers and the colorants are often introduced separately and, in this case, the colorants are free, which can constitute a drawback from the standpoint of safety of the composition; some colorants which would give an especially attractive color cannot, in particular, be used because they display significant toxicity under the conditions of use of the composition: for example, chlorinated phthalocyanine green (codified in the Color Index under no. 74,260) cannot be used for the manufacture of cosmetic compositions where there is a risk of them being in contact with the mucosa of the eyes, since it is toxic under these conditions. Furthermore, for some colorants, it is necessary, for the purpose of using them in cosmetic compositions, to keep a check on their purity with great care in order to avoid any risk of toxicity due to impurities in the colorant.

It has already been proposed to tint the bulk phase of the fillers in order to avoid having free colorants in the composition; nevertheless, the colorant may be partially released by the filler under the conditions of application and, in addition, in order to obtain a sufficiently intense coloration, it is necessary to introduce a relatively large amount of colorants since the whole volume of the filler particles has to be tinted, resulting in an increase in the cost of the composition.

According to the present invention, it has been found that colorants, even ones generally considered to be toxic, may be introduced into cosmetic compositions by introducing at least part of the filler in the form of particles coated with a polymer containing at least one colorant, the full complement of colorants being combined with the polymer coating the filler, instead of introducing the particulate filler and the colorant separately into the cosmetic composition.

The subject of the invention is, consequently, a colored cosmetic composition containing at least one particulate filler and at least one colorant, characterized in that at least part of the fillers of the composition is coated with a polymer combined with at least one colorant.

It is preferable for the full complement of the colorant(s) of the composition to be combined with at least one polymer coating a particulate filler. The particles of the coated filler are preferably between 1 and 200 $\mu$m in size in their smallest dimension.

According to the present invention, the filler is preferably coated with polymer combined with at least one colorant by the process described in FR-A 2,651,789. According to this process, the pulverulent filler is coated using a solution of at least one of the constituents of the finished polymer, the solvent is removed and another constituent of the polymer is then reacted with the coated pulverulent filler. The polymer is thus prepared in situ. The colorant is introduced in suspension or solution form into the solution for coating the filler. In the present description, the term colored polymer will be used hereinafter to denote a polymer containing at least one colorant distributed in its bulk phase in solution or suspension form.

According to FR-A 2,651,789, the solvent is an organic solvent, but it was found that the solvent could also, in some cases, be an aqueous phase.

As explained above, the use in a cosmetic composition of a filler coated with colored polymer enables relatively toxic colorants to be used, and makes it possible to use a smaller amount of colorant in order to obtain a given coloration since all of the colorant is in the coating of the filler particles, and hence at the surface of the said particles, and no longer distributed throughout the volume of the particles, which was the case with the tinted fillers of the prior art. Furthermore, the siting of the colorant in the film of polymer coating enables the light fastness of the colorant to be improved; for example, it has been found that manganese violet (codified in the Color Index (CI) under the reference 77,742) may be used in this way without the color of the cosmetic composition fading in the light. A further advantage is that the presence of the polymer coating the filler enables its density to be modified, and this can, in particular, prevent sedimentation; in addition, the coating can also modify the surface state of the particles: the filler may hence, in this way, become hydrophobic or hydrophilic after coating. The thickness of the film of polymer coating is generally between 0.2 and 50 $\mu$m.

The coated filler(s) according to the invention can be any filler which is usable in the cosmetic field, be it inorganic or organic; before coating, such a filler generally has a particle size of between 0.8 and 180 $\mu$m. Among inorganic fillers, there may be mentioned plaster, calcium carbonate, mica, silica, calcium silicate, kaolin, glass beads, titanium oxide, zinc oxide, zirconium oxide and alumina. Among organic fillers, there may be mentioned cellulose fibres, for example wood dust or cotton fibres, starch, expanded microspheres, for example of polyvinylidene/acrylonitrile copolymer, powdered polyethylene, powdered nylon, powdered silicone, powdered polypropylene, powdered polycarbonate, powdered urea-formaldehyde resin, powdered crosslinked gelatin, powdered collagen, powdered keratin, powdered polystyrene and powdered Teflon. The filler can also consist of any mixture of inorganic and/or organic fillers.

In the composition according to the invention, the colored, coated filler may be mixed with at least one uncolored and/or uncoated filler. The composition can also contain several identical or different fillers coated with different polymers combined with identical or different colorants.

The polymer prepared in situ on the fillers can be any polyaddition polymer in which one of the constituents can be dissolved in the presence of a colorant in order to coat the filler, and the other constituent can be brought into contact with the coated filler in order to form the polymer; it can also be a crosslinkable polymer capable of being dissolved in the presence of a colorant in order to coat the filler, the other constituent then being a crosslinking agent.

Among polymers which can be prepared on the filler, there may be mentioned polyurethanes, epoxy resins, chlorinated polyethers, polyesters, urea-formaldehyde resins and acrylic, methacrylic and vinyl homo- or copolymers.

According to a preferred mode of preparation, the filler is coated using a solution of urethane or of amino-functional silicone as crosslinkable polymer, and a compound chosen from isocyanates is used as crosslinking agent.

The colorants used can naturally be all colorants which are usable in cosmetics, be they inorganic pigments or organic colorants. The colorants are used either in solution form or in the form of a dispersion of solid particles having a particle size of between 0.1 and 25 $\mu$m, in which case the diameter of the colorant particles is less than that of the filler particles before coating.

Among the inorganic pigments generally used in cosmetics, there may be mentioned:

titanium dioxide (rutile or anatase), where appropriate surface-treated (codified in the Color Index under the reference CI 77,891), manganese violet (CI 77,742), ultramarine blue (CI 77,007), chromium oxide (CI 77,288), hydrated chromium oxide (CI 77,289), ferric blue (CI 77,510), zinc oxide, zirconium dioxide.

Among the organic colorants generally used in cosmetics, there may be mentioned:

D & C red no. 19 (CI 45,170),

D & C red no. 9 (CI 15,585),

D & C red no. 21 (CI 45,380),

D & C orange no. 4 (CI 15,510),

D & C orange no. 5 (CI 45,370),

D & C red no. 27 (CI 45,410),

D & C red no. 13 (CI 15,630),

D & C red no. 7 (CI 15,850:1),

D & C red no. 6 (CI 15,850:2),

D & C yellow no. 5 (CI 19,140),

D & C red no. 36 (CI 12,085),

D & C orange no. 10 (CI 45,425),

D & C yellow no. 6 (CI 15,985),

D & C red no. 30 (CI 73,360),

D & C red no. 3 (CI 45,430), carbon black (CI 77,266), cochineal carmine lake (CI 75,470), natural or synthetic melanin, and aluminium lakes.

However, it is also possible, according to the invention, to use, without risk of toxicity, colorants which are considered to be harmful to the mucosa of the eyes and/or to the skin and which have consequently not been generally used until now in cosmetic compositions.

It is possible, according to the invention, to use one or more inorganic and/or organic colorants, combined either with the same filler or with different fillers.

The examples given below, purely by way of illustration and without implied limitation, will enable a better understanding of the invention to be gained.

EXAMPLE 1

Compacted Powder

A first colored, coated filler consists of talc of average particle size 10 $\mu$m coated with a polyurethane film having a thickness of approximately 2 $\mu$m and containing 2% by weight of ultramarine blue (CI 77,007) of particles size approximately 0.2 $\mu$m.

A second colored, coated filler consists of mica of average particle size 10 $\mu$m coated with an epoxy resin film of thickness approximately 3 $\mu$m and containing ferric blue (CI 77,510) having a particle size of approximately 0.5 $\mu$m.

A mixture is prepared containing (in % by weight):

| | |
|---|---|
| 1st colored, coated filler defined above | 40% |
| 2nd colored, coated filler defined above | 20% |
| Titanium dioxide | 20% |
| Mica | 5% |
| Isopropyl myristate | 2% |
| Liquid paraffin | 2% |
| Microspheres of expanded polyacrylate, sold under the tradename "EXPANCELL 551 DE 20" by the company "CASCO NOBEL" | 0.5% |
| Sorbitol | 0.5% |
| Talc | 10% |

The mixture is compacted. This Chinese blue-colored compacted powder may be applied using a powder puff or a brush. This powder is found to display exceptional stability of hue.

EXAMPLE 2

Loose Powder to be Applied with a Powder Puff

A mixture having the following composition is used:

| | |
|---|---|
| Filler consisting of powdered nylon sold under the tradename "ORGASOL 2002 D" by the company "ATOCHEM" (particle size approximately 10 $\mu$m), coated with a 2 $\mu$m layer of acrylic copolymer containing 2% by weight of colorants consisting of yellow and black iron oxides and D & C Red 30 in the proportions 4:2:1 (particle size approximately 0.5 $\mu$m) | 37.75% |
| Mica | 55.45% |
| Hollow microspheres of vinylidene chloride/acrylonitrile type copolymer, marketed under the name "EXPANCEL 551 DE" by the company "CASCO NOBEL" | 1% |
| Magnesium myristate | 2% |
| Liquid paraffin | 3% |
| Perfume | 0.8% |

The powder is prepared in the following manner: mica, coated filler and magnesium myristate are mixed and then ground. The ground preparation is thereafter sprayed with perfume, and liquid paraffin is then added. "EXPANCEL 551 DE" is finally added using simple mixing. A golden peach-colored loose powder is obtained.

EXAMPLE 3

Nail Varnish

A filler is used consisting of a powdered $CaCO_3$ of particle size in the region of 12 $\mu$m, previously coated with an epoxy resin forming an approximately 3 $\mu$m layer in which pigments having a particle size of 2 to 5 $\mu$m are trapped at a concentration of 4% by weight in the following proportions (by weight): $TiO_2$=100, black iron oxide=10, red iron oxide=5, D & C Red no. 6 (Ba lake)=10.

The nail varnish prepared has the following composition (in % by weight).

| | |
|---|---|
| n-Butyl acetate | 25% |
| Toluene | 25% |
| Ethyl acetate | 10% |
| Isopropylalcohol | 6.75% |
| Bentone 27 (montmorillonite) | 1% |

-continued

| | |
|---|---|
| Nitrocellulose | 16% |
| Toluenesulphonamide-formaldehyde resin | 9% |
| Dibutyl phthalate | 5% |
| Camphor | 1% |
| Colored, coated filler defined above | 1.25% |

An old rose-colored nail varnish having non-irreversible sedimentation, possessing good color stability and an absence of migration of the colorants on the nails, is obtained.

In addition, this composition has the advantage of not staining the nail when the user removes the varnish by means of a solvent.

We claim:

1. A colored cosmetic composition comprising a particulate filler and a colorant, at least a portion of said particulate filler being coated with a polymer combined with said colorant, said particulate filler having a particle size ranging from 0.8 to 180 µm and being selected from the group consisting of (a) an inorganic filler selected from the group consisting of plaster, calcium carbonate, mica, silica, calcium silicate, kaolin, glass beads, titanium oxide, zinc oxide, zirconium oxide, alumina and mixtures thereof, and (b) an organic filler selected from the group consisting a cellulose fiber, starch, polyvinylidene/acrylonitrile copolymer, powdered polyethylene, powdered nylon, powdered silicone, powdered polypropylene, powdered polycarbonate, powdered urea-formaldehyde resin, powdered crosslinked gelatin, powdered collagen, powdered keratin, powdered polystyrene, powdered Teflon and mixtures thereof, said polymer being selected from the group consisting of a polyurethane and an epoxy resin, said colorant having a particle size ranging from 0.1 to 25 µm and being selected from the group consisting of (a) an inorganic pigment selected from the group consisting of titanium dioxide, manganese violet, ultramarine blue, chromium oxide, hydrated chromium oxide, ferric blue, zinc oxide, zirconium dioxide and mixtures thereof and (b) an organic colorant selected from the group consisting of CI 45,170, CI 15,585, CI 45,380, CI 15,510, CI 45,370, CI 45,410, CI 15,630, CI 15,850:1, CI 15,850:2, CI 19,140, CI 12,085, CI 45,425, CI 15,985, CI 73,360, CI 45,430, CI 77,266, CI 75,470, natural melanin, synthetic melanin, an aluminum lake and mixtures thereof.

* * * * *